United States Patent
Funabasama et al.

(10) Patent No.: US 8,724,869 B2
(45) Date of Patent: May 13, 2014

(54) MEDICAL IMAGE PROCESSING APPARATUS

(75) Inventors: Shintaro Funabasama, Utsunomiya (JP); Tatsuo Maeda, Nasushiobarashi (JP); Yasuko Fujisawa, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 290 days.

(21) Appl. No.: 13/356,155

(22) Filed: Jan. 23, 2012

(65) Prior Publication Data
US 2012/0121145 A1 May 17, 2012

Related U.S. Application Data

(63) Continuation of application No. PCT/JP2011/069953, filed on Sep. 1, 2011.

(30) Foreign Application Priority Data

Sep. 1, 2010 (JP) .................................. 2010-196047

(51) Int. Cl.
*G06K 9/00* (2006.01)

(52) U.S. Cl.
USPC .......................................................... 382/128

(58) Field of Classification Search
None
See application file for complete search history.

(56) References Cited

U.S. PATENT DOCUMENTS

| 7,054,406 | B2 * | 5/2006 | Ikeda et al. ........................ 378/8 |
| 2003/0097076 | A1 * | 5/2003 | Nambu et al. .................. 600/504 |
| 2004/0114706 | A1 * | 6/2004 | Ikeda et al. ........................ 378/4 |
| 2004/0218794 | A1 * | 11/2004 | Kao et al. ........................ 382/128 |
| 2004/0242994 | A1 * | 12/2004 | Brady et al. ..................... 600/420 |
| 2005/0058331 | A1 * | 3/2005 | Klotz ............................... 382/131 |
| 2006/0004279 | A1 * | 1/2006 | Ikeda et al. ..................... 600/411 |
| 2010/0080757 | A1 * | 4/2010 | Haaga et al. ..................... 424/9.3 |
| 2011/0150309 | A1 * | 6/2011 | Barfett et al. .................. 382/131 |
| 2011/0176710 | A1 * | 7/2011 | Mattiuzzi et al. ............. 382/128 |
| 2012/0141005 | A1 * | 6/2012 | Djeridane et al. ............. 382/131 |

FOREIGN PATENT DOCUMENTS

JP 2003-116843 A 4/2003

(Continued)

OTHER PUBLICATIONS

Diego J. Covarrubias,a Bruce R. Rosen,b Michael H. Lev. "Dynamic Magnetic Resonance Perfusion Imaging of Brain Tumors" The Oncologist , 9:528-53. 2004.*

Robert G. Sheiman, MD, BSChE Arkadiusz Sitek, PhD. "Feasibility of Measurement of Pancreatic Perfusion Parameters with Single Compartment Kinetic Model Applied to Dynamic Contrast enhanced CT images" Radiology, vol. 249: No. 3—Dec. 2008.*

(Continued)

*Primary Examiner* — Barry Drennan
*Assistant Examiner* — Oneal R Mistry
(74) *Attorney, Agent, or Firm* — Yoshida & Associates, LLC

(57) ABSTRACT

An apparatus handles a series of medical images. A time density curve generation unit generates time density curves respectively corresponding to pixels from the series of medical images. An approximation processing unit approximates a convolution between a specific time density curve of the time density curves and each of types of kinetic models to each of the time density curves upon adjustment of at least one parameter which each of the kinetic models has. A suitability index map generation unit generates types of suitability index maps respectively corresponding to the types of kinetic models based on approximation errors respectively corresponding to the pixels, which are obtained by the approximation processing unit.

13 Claims, 13 Drawing Sheets

(56) References Cited

FOREIGN PATENT DOCUMENTS

| | | |
|---|---|---|
| JP | 2003-190148 A | 7/2003 |
| JP | 2003-325472 A | 11/2003 |
| JP | 2005-95340 A | 4/2005 |
| JP | 2007-144139 A | 6/2007 |
| JP | 2007-526071 A | 9/2007 |
| JP | 2008-100121 A | 5/2008 |
| JP | 2010-213760 A | 9/2010 |
| WO | 2009/112538 A1 | 9/2009 |

OTHER PUBLICATIONS

The International Search Report corresponding to International Application No. PCT/JP2011/0699553 mailed on Oct. 4, 2011.

The International Search Report corresponding to International Application No. PCT/JP2011/0699553 mailed on Mar. 21, 2013.

International Search Report corresponding to International Application No. PCT/JP2011/0699553 mailed on Oct. 4, 2011.

* cited by examiner

Region map

Three types of perfusion analysis maps are combined into one perfusion analysis map

MEDICAL IMAGE PROCESSING APPARATUS

CROSS REFERENCE TO RELATED APPLICATIONS

This application is a Continuation Application of PCT Application No. PCT/JP2011/069953, filed Sep. 1, 2011 and based upon and claiming the benefit of priority from prior Japanese Patent Application No. 2010-196047, filed Sep. 1, 2010, the entire contents of all of which are incorporated herein by reference.

FIELD

Embodiments described herein relate generally to a medical image processing apparatus.

BACKGROUND

The analysis of blood flow perfusion (Perfusion) is very effective for the functional diagnosis of organs. Perfusion analysis includes approximately identifying the transfer coefficient between a time density curve (TDC) associated with an artery inflowing into an organ and a time density curve associated with an organ tissue by, for example, the least squares method and calculating a perfusion index from the identified transfer coefficient.

For example, unlike perfusion analysis on the brain, analysis on feading and functional blood vessels of abdominal organs is performed by using various kinds of combinations of kinetic models and analysis models selected from a plurality of types of kinetic models (compartment models) and a plurality of types of analysis models in accordance with target organs, because feading and functional blood vessels vary for each organ.

Therefore, a kinetic index exhibits low suitability in a region other than an organ region corresponding to a selected kinetic model and analysis model. Although it is necessary to exclude such a region from perfusion diagnosis, it is not possible to clearly recognize the region. In general, since a tissue in an abdominal region is an assembly of soft tissues exhibiting small CT value differences, the suitability of even an organ region segmented from a CT image is not high.

CITATION LIST

Patent Literature

Patent Literature 1: Japanese Patent Laid-Open No. 2007-144139

DETAILED DESCRIPTION

Figure 1:
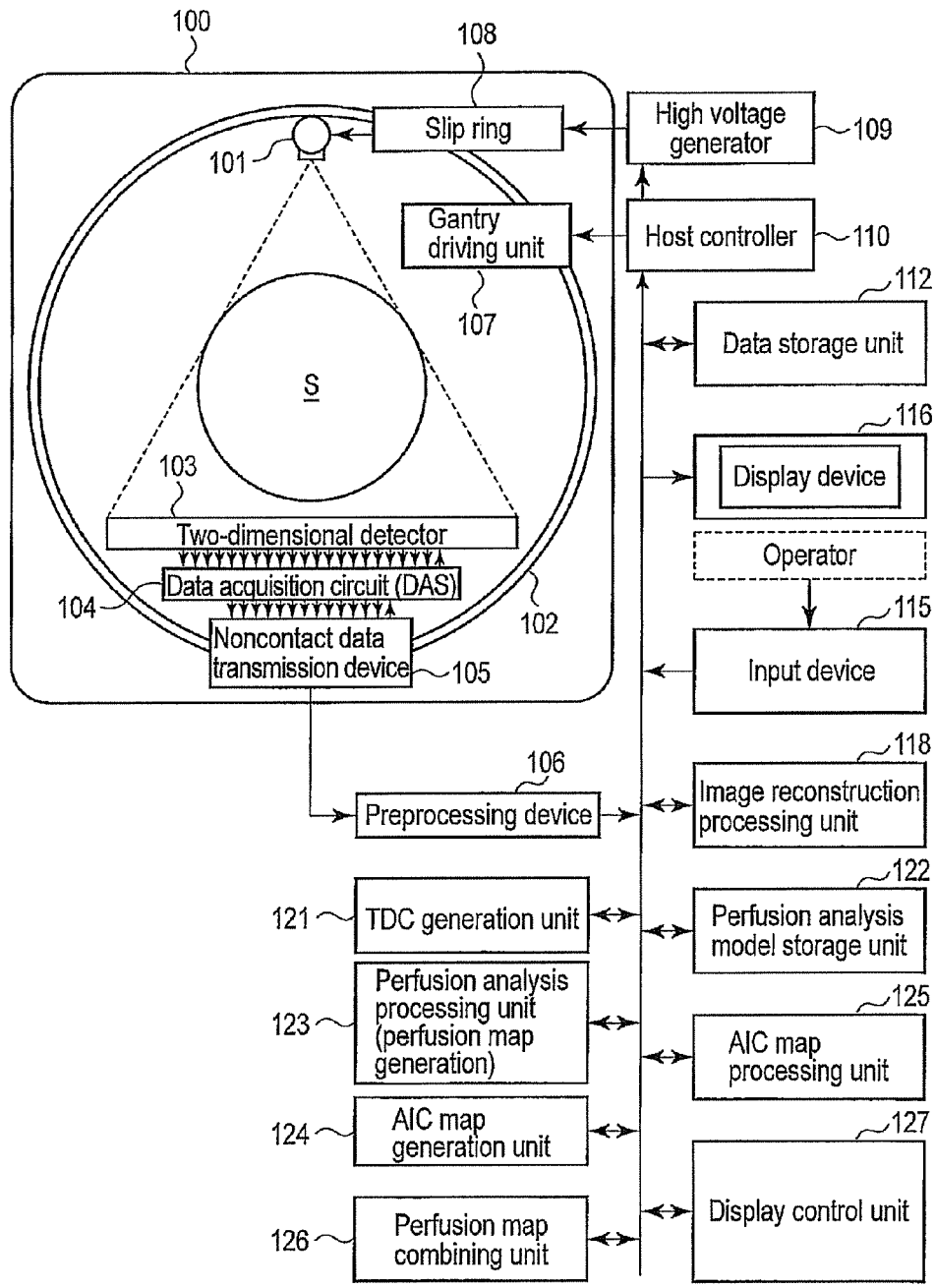
FIG. 1 is a view showing the arrangement of an X-ray computed tomography apparatus including a medical image processing apparatus according to this embodiment.

In general, according to one embodiment, a medical image processing apparatus handles the data of a series of medical images associated with an object. A time density curve generation unit generates a plurality of time density curves respectively corresponding to a plurality of pixels from the series of medical images. An approximation processing unit approximates a convolution between a specific time density curve of the plurality of time density curves and each of a plurality of types of kinetic models to each of the plurality of time density curves upon adjustment of at least one parameter which each of the kinetic models has. A suitability index map generation unit generates a plurality of types of suitability index maps respectively corresponding to the plurality of types of kinetic models based on a plurality of approximation errors respectively corresponding to the plurality of pixels, which are obtained by the approximation processing unit.

A medical image processing apparatus according to this embodiment will be described below with reference to the accompanying drawings. The medical image processing apparatus according to the embodiment handles the data of a series of medical images obtained by imaging the same region of an object a plurality of number of times for various periods of time, i.e., dynamic scanning or cine scanning. A time density curve generation unit generates a plurality of time density curves respectively corresponding to a plurality of pixels from a series of medical images. An approximation processing unit approximates a convolution between a specific time density curve of the plurality of time density curves and each of a plurality of response functions respectively having a plurality of shapes suited to a plurality of types of kinetic models to each of the plurality of time density curves upon adjustment of at least one parameter which each of the kinetic models has. A suitability index map generation unit generates a plurality of types of suitability index maps respectively corresponding to the plurality of types of kinetic models based on a plurality of approximation errors respectively corresponding to the plurality of pixels, which are obtained by the approximation processing unit.

This embodiment relates to a technical field in which an index indicating the hemodynamics of an organ tissue for each pixel, i.e., a perfusion index, is calculated from a series of a plurality of medical images temporally continuously acquired mainly in association with an arbitrary region of an object, typically an abdominal region assumed to exhibit most the functioning effect of the embodiment, and then a perfusion map as a spatial distribution of perfusion indices is generated. Medical images to be handled in this embodiment are not limited to tomographic images obtained by an X-ray computed tomography apparatus, and may include medical images acquired by any modalities including a single photon emission tomography apparatus (SPECT), positron emission tomography apparatus (PET), magnetic resonance imaging apparatus (MRI), and ultrasonic diagnostic apparatus. The embodiment will exemplify a case in which tomographic images obtained by an X-ray computed tomography apparatus are handled.

FIG. 1 shows both a medical image processing apparatus according to this embodiment and an X-ray computed tomography apparatus. A gantry unit 100 includes a rotatably supported rotating ring 102. An X-ray tube 101, a high voltage generator 109, a two-dimensional detector 103, and a data acquisition circuit 104 (DAS: Data Acquisition System) are mounted on the rotating ring 102. The high voltage generator 109 is connected to the X-ray tube 101 via a slip ring mechanism 108. A preprocessing device 106 is connected to the data acquisition circuit 104 via a noncontact data transmission device 105 using an optical or electromagnetic element. The preprocessing device 106 converts the raw data output from the data acquisition circuit 104 into projection data by analog/digital conversion processing and various types of correction processing. A data storage unit 112 stores projection data. An image reconstruction processing unit 118 reconstructs tomographic image data based on the projection data. The data storage unit 112 stores the tomographic image data. Note that in this embodiment, so-called dynamic scanning is executed for an abdominal region of an object as an imaging target by continuously rotating the rotating ring 102 under the control of a host controller 110. This generates the data of a series of a plurality of tomographic images temporally continuously acquired in association with the same slice of the abdominal region of the object. The data storage unit 112 stores the generated data.

Figure 4:
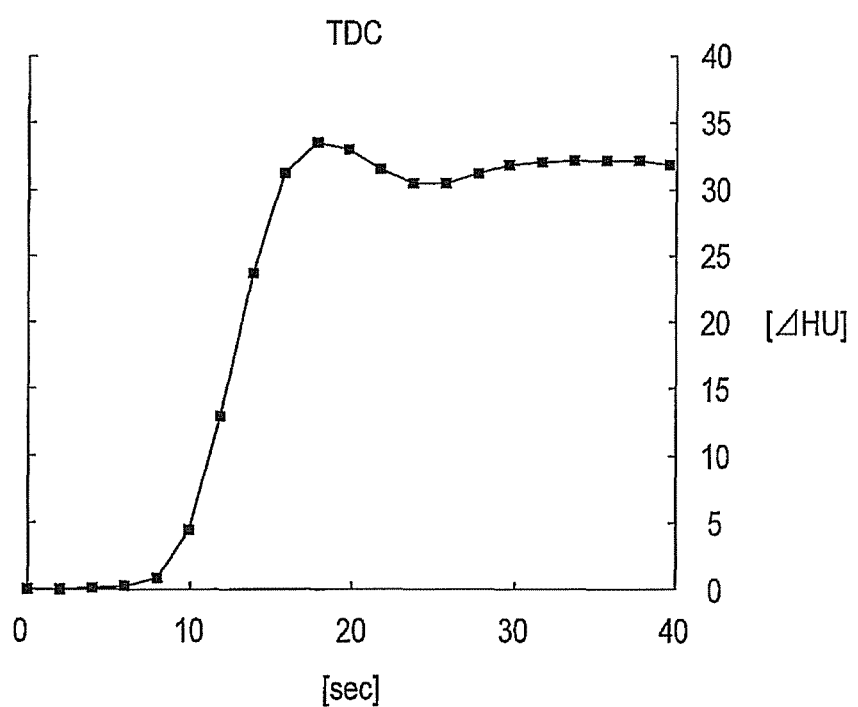
FIG. 4 is a graph showing an example of the TDC generated in step S13 in FIG. 2.
Figure 5:
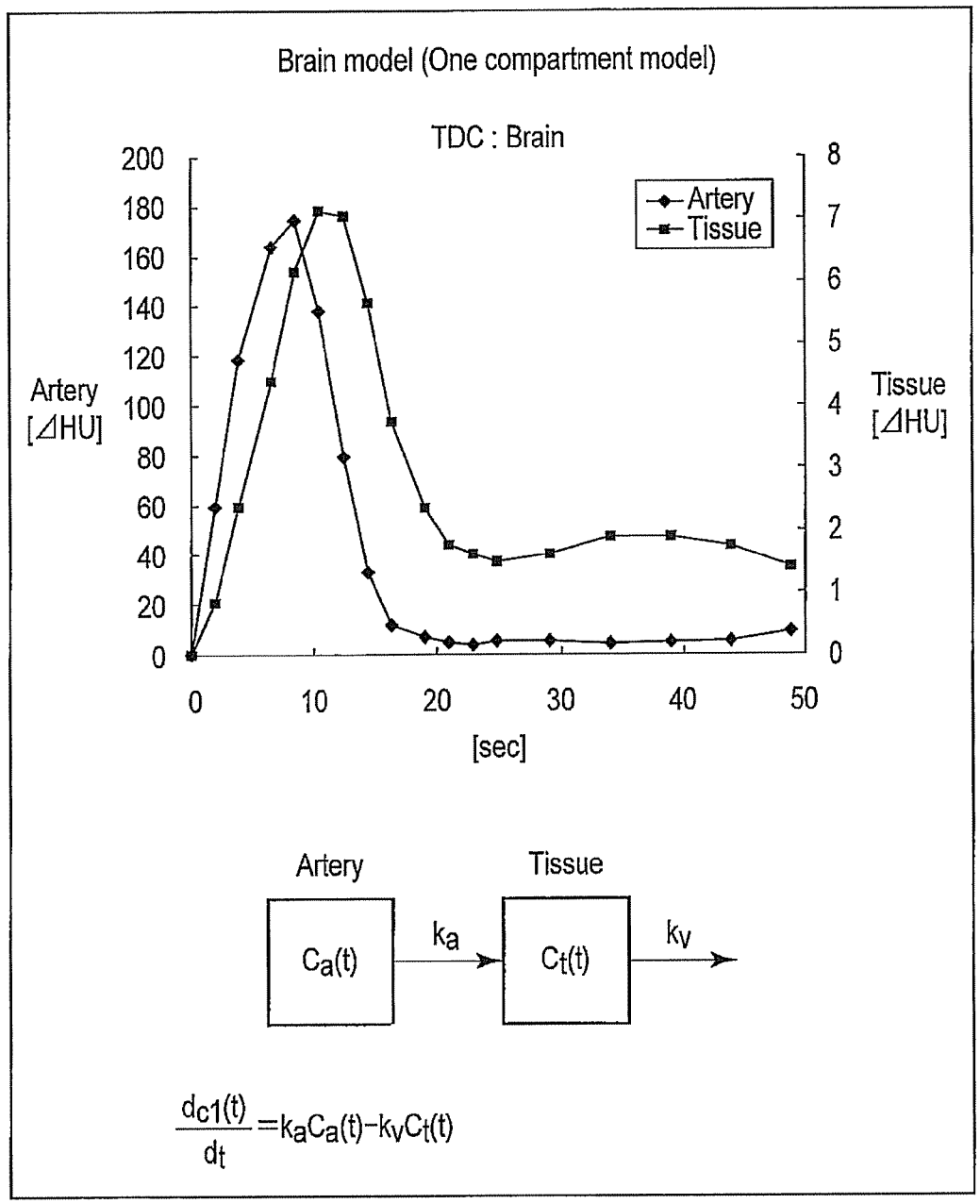
FIG. 5 is a view showing a brain model (One compartment model) stored in a perfusion analysis model storage unit in FIG. 1.
Figure 6:
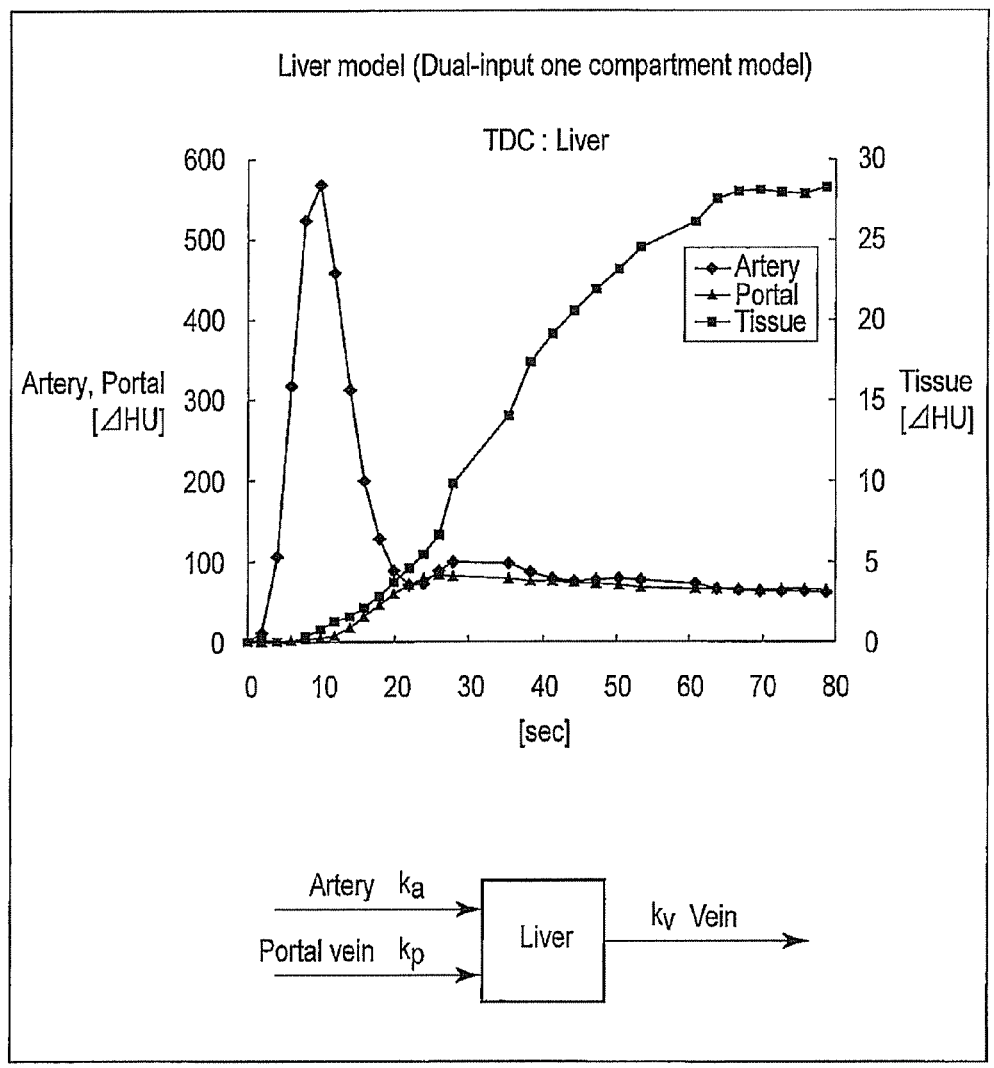
FIG. 6 is a view showing a liver model (Dual-input one compartment model) stored in the perfusion analysis model storage unit in FIG. 1.
Figure 7:
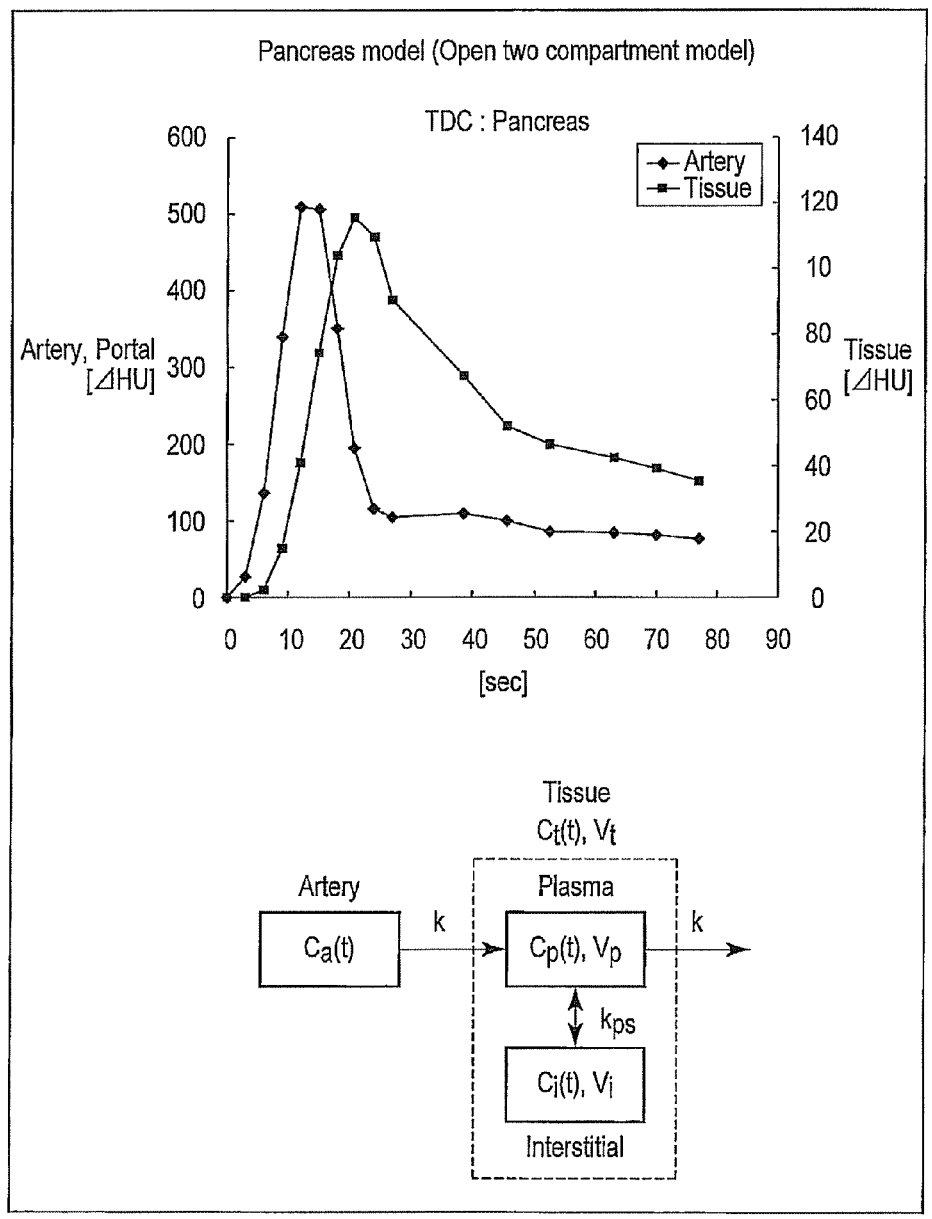
FIG. 7 is a view showing a pancreas model (Open two compartment model) stored in the perfusion analysis model storage unit in FIG. 1.
Figure 8:
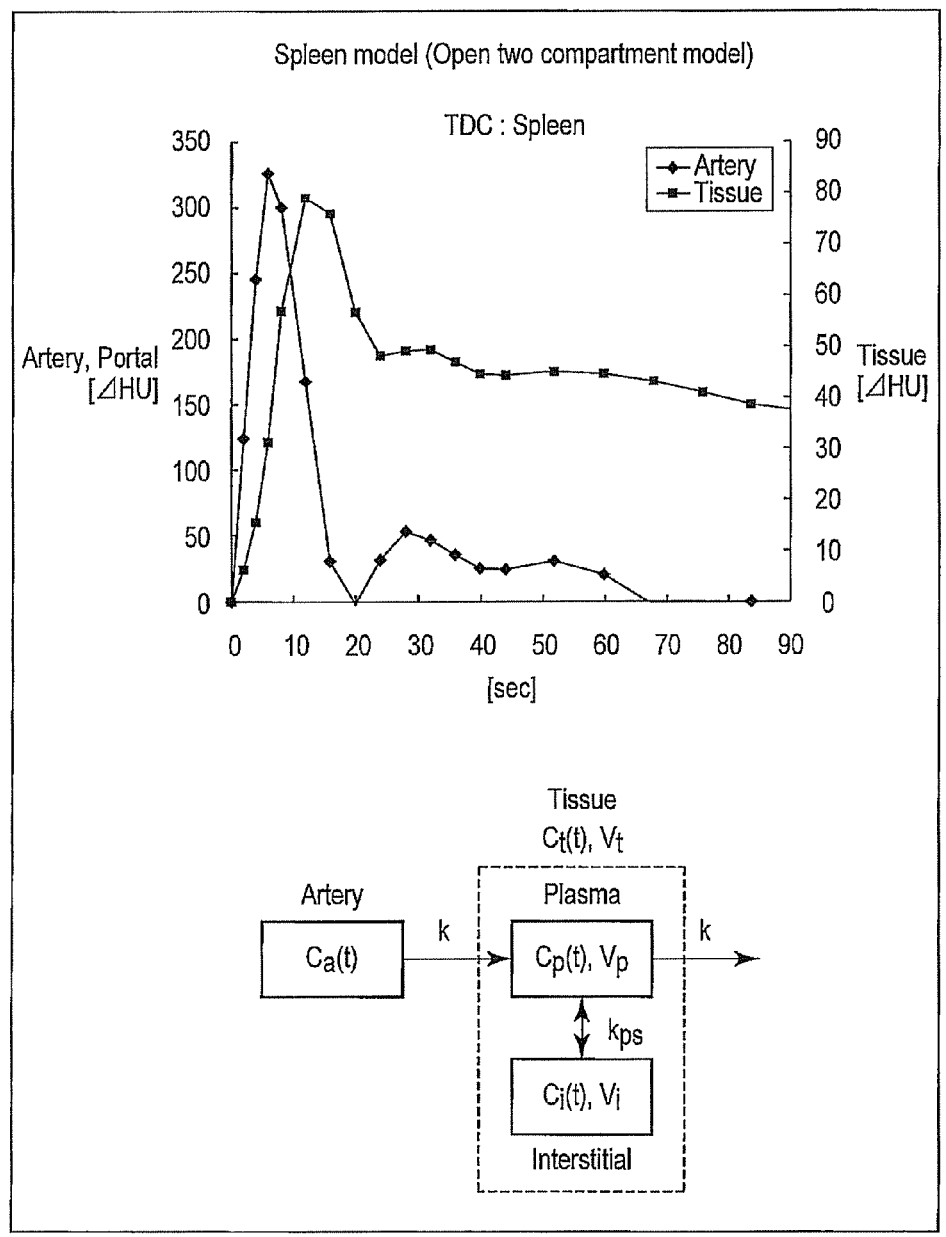
FIG. 8 is a view showing a spleen model (Open two compartment model) stored in the perfusion analysis model storage unit in FIG. 1.
Figure 9:
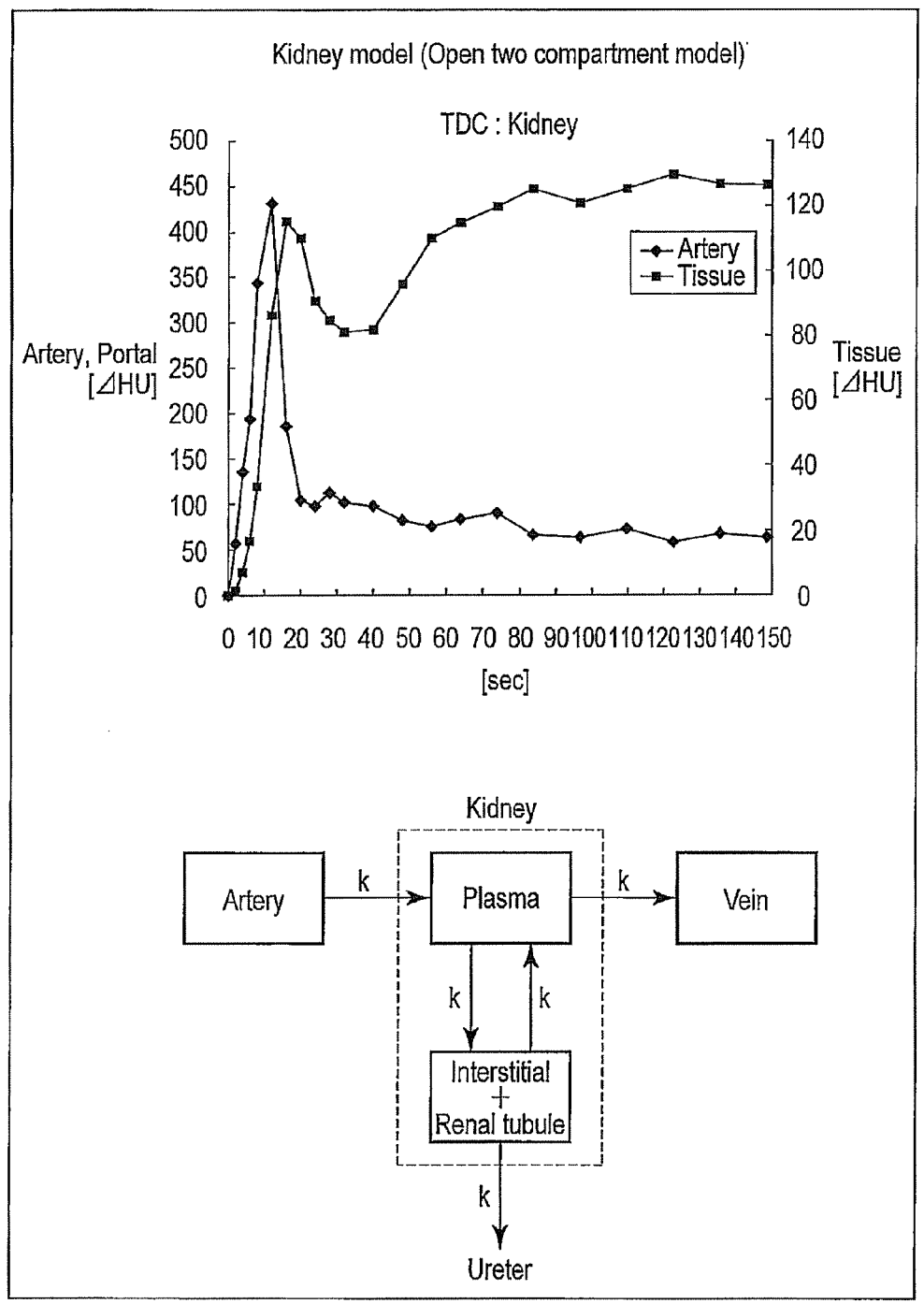
FIG. 9 is a view showing a kidney model (Open two compartment model) stored in the perfusion analysis model storage unit in FIG. 1.

The medical image processing apparatus according to this embodiment includes the following constituent elements in addition to the data storage unit 112. A TDC generation unit 121 generates temporal changes in CT value exemplified in FIG. 4, generally a time density curve (TDC), for each pixel from the data of the series of tomographic images. The data storage unit 112 stores TDC data. A perfusion analysis model storage unit 122 associates a plurality of types of perfusion analysis models with a plurality of organs contained in an object, respectively.

FIGS. 5 to 9 each show an example of a perfusion analysis model. Perfusion analysis models are classified into a plurality of types including "One compartment model", "Dual-input one compartment model", "Open two compartment model", and "Leakage open two compartment model" from the viewpoints of the number of compartments on hemodynamics in a single organ (compartment), the inflow blood vessel count (input) of the organ, the presence/absence of interstitiality between compartments in the organ (Open), and the presence/absence of leakage from any portion other than the blood vessels of the organ (leakage). A normal brain tissue can be assumed to be "One compartment model" since the blood-brain barrier (BBB) prevents a contrast medium from flowing outside blood vessels. The liver is constituted by "Input curve" including two blood vessels, i.e., an artery and a portal vein, and hence can be assumed to be fitted to "Dual-input one compartment model". A pancreas region is an organ from which a contrast medium flows out very quickly. Ignoring "Interstitial", this region may be easily analyzed with "One compartment model". However, "Two compartment model" is considered to be the most prospective model. A spleen region allows a contrast medium to freely flow between intravascular fluid (Plasma) and extravascular fluid (Interstitial), and hence can be assumed to be fitted to "Open two compartment model". A uterine tumor region allows a contrast medium to freely flow between intravascular fluid (Plasma) and extravascular fluid (Interstitial), and hence can be assumed to be fitted to "Open two compartment model". A neck tumor region allows a contrast medium to freely flow between intravascular fluid (Plasma) and extravascular fluid (Interstitial), and hence can be assumed to be fitted to "Open two compartment model".

Perfusion analysis requires to specify the positions of inflow and outflow blood vessels for each organ. The perfusion analysis model storage unit 122 associates information about the position of an inflow blood vessel for each organ with a corresponding one of a plurality of organs. For example, in the case of the liver, information about an artery, portal vein, and vein is associated with the organ. The operator can designate inflow and outflow blood vessels on the image in accordance with the information specifying the inflow and outflow blood vessels.

A perfusion analysis processing unit 123 generates a plurality of perfusion maps respectively corresponding to a plurality of kinetic models by using the data of a series of tomographic images, the information of inflow and outflow blood vessels, and a plurality of kinetic models specified in advance. Each kinetic model is a response function defining the relationship between temporal changes in the inflow rate of blood into the corresponding organ and temporal changes in blood flow rate in the tissue in the organ. A plurality of response functions have a plurality of shapes respectively suited to a plurality of kinetic models. In the following description, "transfer function" will be handled as a representative example of a response function. Each transfer function has at least one parameter. The inflow of blood into each organ is given by a time density curve associated with a specific pixel on an artery in a tomographic image or an average time density curve associated with a specific pixel and its surrounding pixels. Temporal changes in blood flow rate associated with the tissue in the organ are given by a time density curve associated with each of a plurality of pixels on the tissue in the organ. A time density curve associated with a specific pixel is obtained by convoluting transfer functions linearly or nonlinearly in the time direction. In this embodiment, the convoluted time density curve is approximated to the time density curve of each of all the pixels in the image. That is, the parameter of the transfer function is adjusted to minimize the error between two time density curves. The smaller this approximation error, the higher the suitability to the transfer function. The tissue of a pixel which exhibits high suitability is highly likely to be a tissue in the organ corresponding to the transfer function. The larger the approximation error, the lower the suitability to the corresponding transfer function. The tissue of a pixel which exhibits low suitability is not likely to be a tissue in the organ corresponding to the transfer function. A plurality of transfer functions are respectively determined in accordance with a plurality of types of organs.

Each transfer function is constructed in accordance with the input/output mechanism of a blood flow in the corresponding organ. A plurality of transfer functions have basic shapes different from each other. Even if the parameter of a given transfer function is changed, its basic shape is maintained. The blood flow mechanism of a given organ is expressed by a transfer function as a single rectangular function. The blood flow mechanism of another organ is expressed by a transfer function obtained by combining a plurality of functions such as a rectangular function and a natural function. The blood flow mechanisms of various organs will be described later.

Note that temporal changes in the density of blood flowing into an organ, which serve as an input function used for approximation processing, are typically generated from a series of tomographic images. However, the present invention is not limited to this. It is possible to prepare in advance standard temporal density changes for organs to which the respective models correspond, and to approximate the convolutions between the standard temporal density changes and transfer functions to temporal density changes generated for each pixel from a series of tomographic images. In this case, approximation errors indicate deteriorations in the functions of the organs.

Assume that a time density curve associated with a specific pixel on an artery is an input function Ca(t), a time density curve of a tissue associated with all the pixels is an output function Ct(t), a transfer function is MTF, and convolution processing is *. A parameter is decided for MTF so as to approximate Ca(t)*MTF to Ct(t), i.e., minimize the least square sum of the error of Ca(t)*MTF with respect to Ct(t). For example, perfusion indices (CBP, CBV, and MTT) representing the hemodynamics of a brain tissue are calculated from the transfer function MTF for which the parameter has been decided. CBP represents a blood flow rate [mL/100 mL/min] per unit volume in a capillary of the brain tissue and per unit time, CBV represents a blood flow rate [mL/100 mL] per unit volume in the brain tissue, and MTT represents the mean transit time [sec] of blood in the capillary.

When using a liver model and a spleen model, the perfusion analysis processing unit 123 performs perfusion analysis processing to generate a spatial model (a perfusion map associated with the liver model) based on a perfusion index which has analyzed each of all the pixels in an analysis target medical image by using the liver model, and to generate a spatial model (a perfusion map associated with the spleen model) based on a perfusion index which has analyzed each of all the pixels by using the spleen model. The perfusion analysis processing unit 123 also generates, for each kinetic model, a residual map associated with the total sum of errors or the square root of the square sum of errors (residuals) when approximating a transfer function, by perfusion analysis processing. The perfusion analysis processing unit 123 generates a plurality of residual maps, together with a plurality of perfusion maps corresponding to a plurality of organs included in a region in the perfusion analysis processing.

An AIC map generation unit 124 generates a plurality of AIC maps respectively corresponding to a plurality of residual maps from the residual maps corresponding to a plurality of organs included in the region. AIC is an example of a statistical suitability index associated with a perfusion index, which is calculated based on errors in approximation processing for perfusion analysis. An AIC map is the spatial distribution of AICs. AIC is an abbreviation for an information criterion, which includes, for example, an Akaike's information criterion and Bayesian information criterion. For example, an Akaike's information criterion is given as follows:

$$AIC = -2 \cdot (\text{maximum logarithmic likelihood} - \text{free parameter count})$$

A free parameter count is a constant in the least squares method. The lower the value of AIC, the higher the suitability, and it can almost be certified that the suitability is high. That is, a region corresponding a lower AIC value in an AIC map exhibits high suitability to a kinetic model used for the perfusion analysis, and a region corresponding to a high AIC value exhibits low suitability to the kinetic model used for the perfusion analysis.

An AIC map processing unit 125 selects a value exhibiting the highest suitability, that is, a minimum value (minimum AIC) in this case, for each pixel from a plurality of AIC maps respectively corresponding to a plurality of organs, and generates a single minimum AIC map representing a spatial distribution having the selected minimum AIC value as a pixel value. The AIC map processing unit 125 performs clustering/labeling processing and contour extraction processing for the minimum AIC map to identify blood vessels and the respective organ regions and generate a region map in which the blood vessels and the organ regions are segmented.

A perfusion map combining unit 126 generates a single perfusion map (composite perfusion map) by partly pasting a plurality of perfusion maps in accordance with the region map generated by the AIC map processing unit 125. In other words, the composite perfusion map indicates a spatial distribution associated with perfusion indices exhibiting high suitability to the respective kinetic models.

A display control unit 127 performs processing required to display a composite perfusion map on a display device 116. The display control unit 127 also performs processing corresponding to the display form of a composite perfusion map in accordance with a command associated with the type of display input from the operator via an input device 115.

Figure 2:
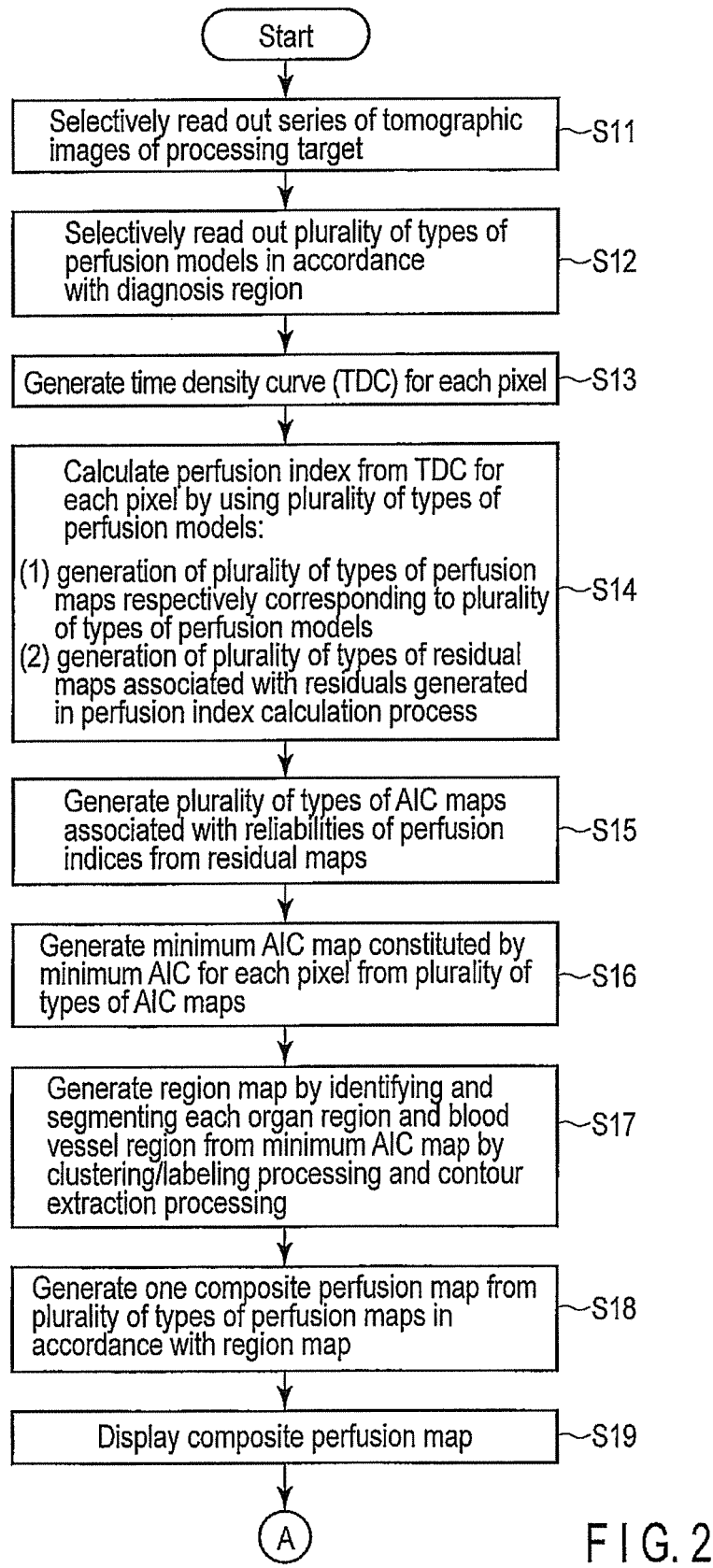
FIG. 2 is a flowchart showing an image processing procedure performed by this embodiment.
Figure 3:
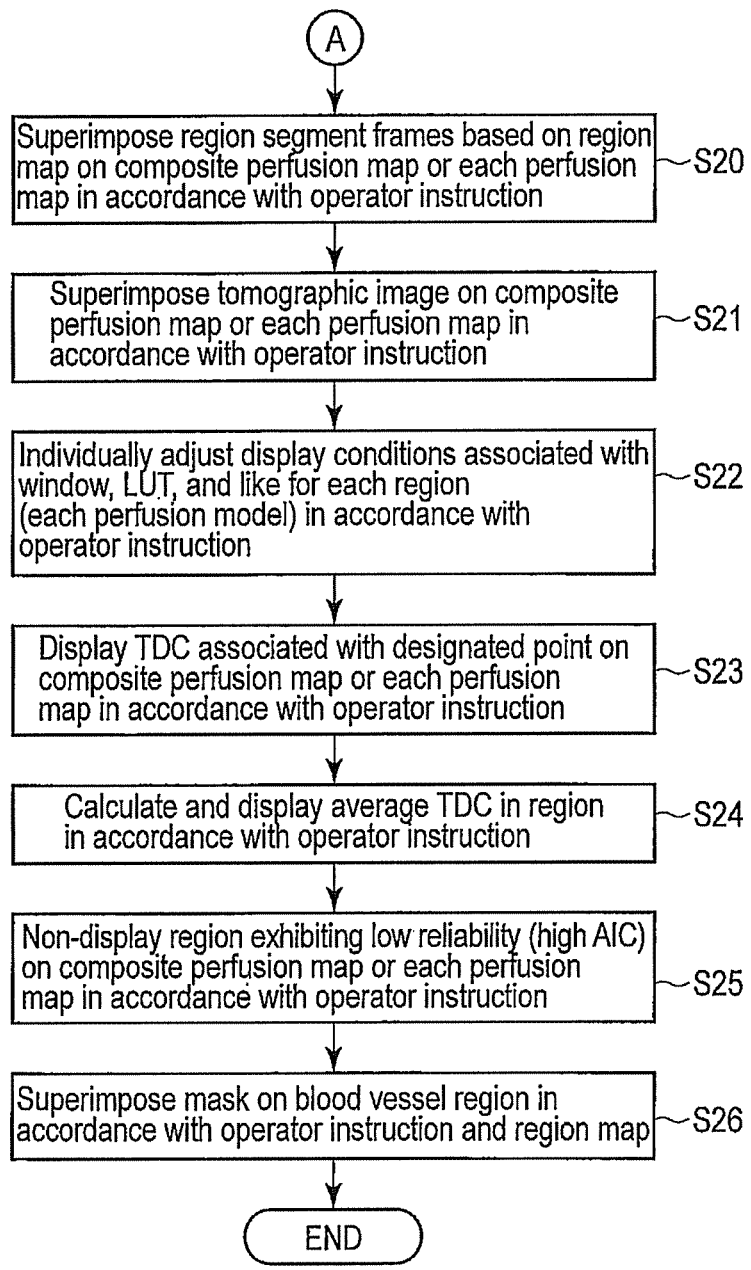
FIG. 3 is a flowchart showing an image processing procedure following the procedure in FIG. 2, which is performed by this embodiment.

FIGS. 2 and 3 show a procedure for perfusion analysis processing by this embodiment. The TDC generation unit 121 reads out the data of a specific series of tomographic images as a perfusion processing target from the data storage unit 112 in accordance with a command input by the operator via the input device 115 (S11). The perfusion analysis processing unit 123 reads out the data of a plurality of kinetic models associated with a plurality of organs corresponding to a diagnosis region belonging to the data of the series of tomographic images, e.g., an abdominal region, from the perfusion analysis model storage unit 122 (S12). For the sake of descriptive convenience, assume that a liver model and spleen model are read out. A plurality of time density curves (TDCs) associated with all the pixels and generated by the TDC generation unit 121 from the series of tomographic images are supplied to the perfusion analysis processing unit 123 (S13).

Figure 10:
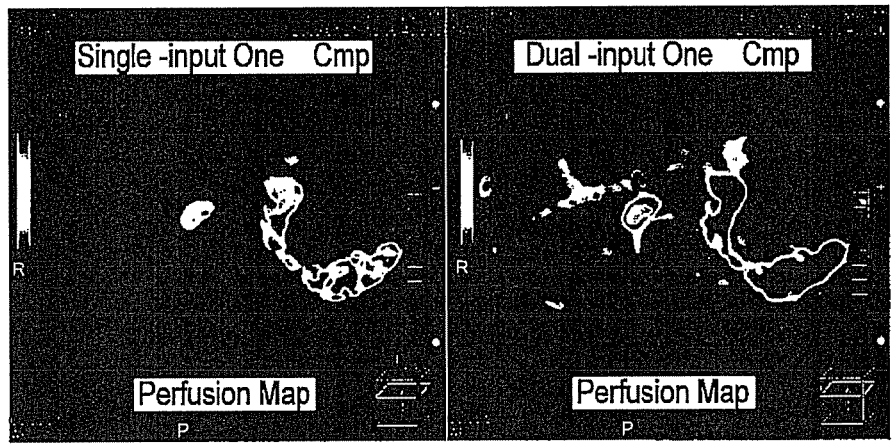
FIG. 10 is a view showing an example of a perfusion map using the spleen model generated in step S14 in FIG. 2 and an example of a perfusion map using the liver model.

The perfusion analysis processing unit 123 generates a perfusion map (see FIG. 10) corresponding to the liver model based on a plurality of time density curves (TDCs) associated with all the pixels using the liver model (S14). In addition, the perfusion analysis processing unit 123 generates a residual map corresponding to the liver model. Likewise, the perfusion analysis processing unit 123 generates a perfusion map corresponding to the spleen model based on a plurality of time density curves (TDCs) associated with all the pixels by using the spleen model, and generates a residual map corresponding to the spleen model.

Figure 11:
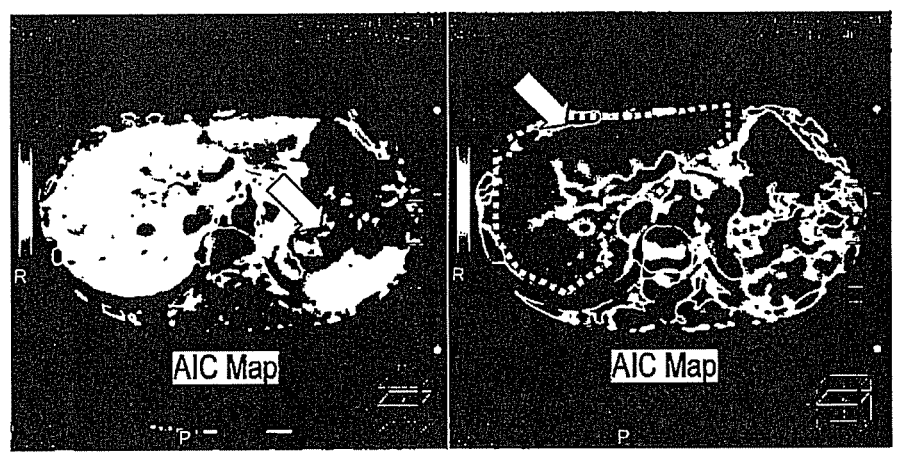
FIG. 11 is a view showing an example of an AIC (An Information Criterion) map using the spleen model generated in step S15 in FIG. 2 and an example of an AIC map using the liver model.
Figure 12:
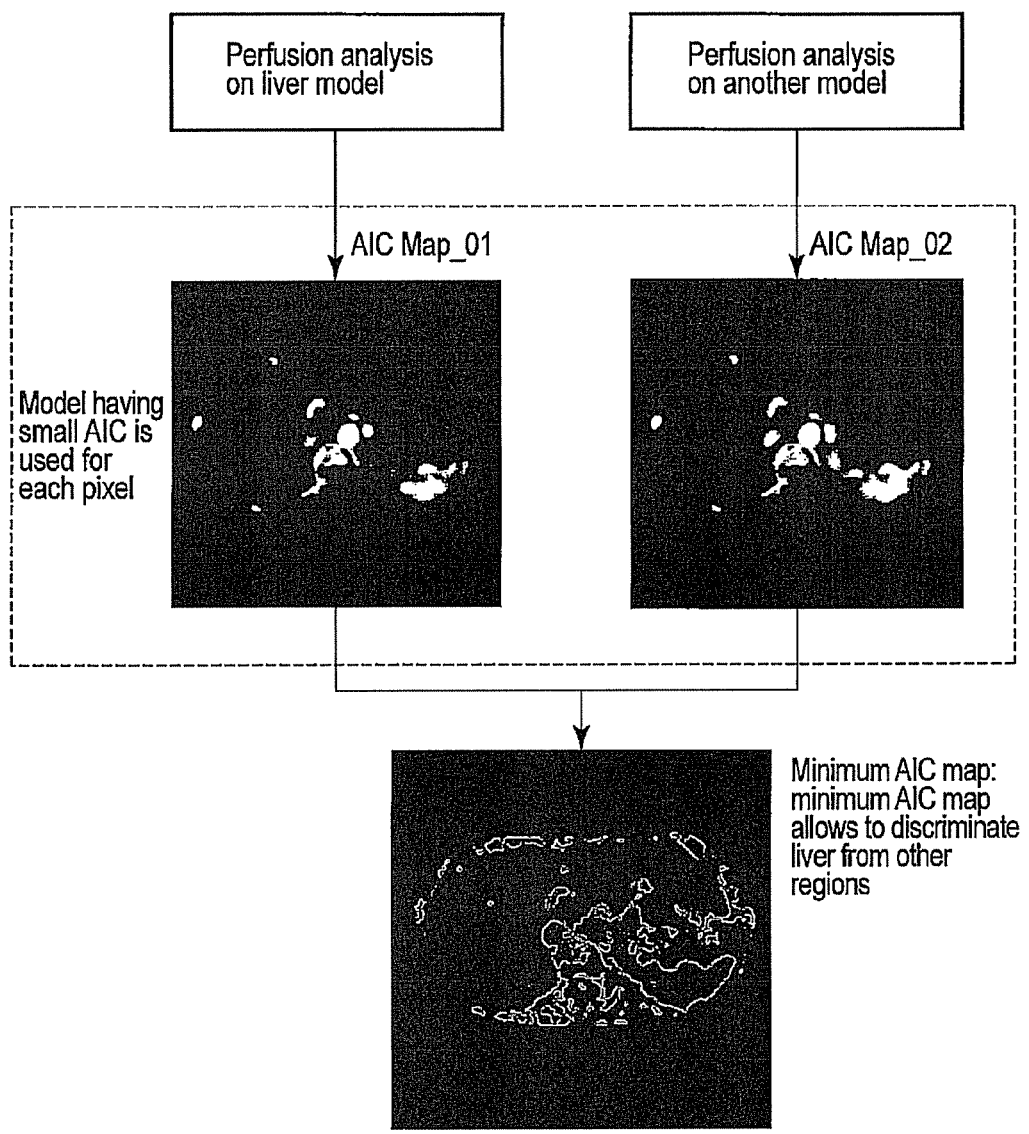
FIG. 12 is a view showing an example of the minimum AIC map generated in step S16 in FIG. 2.
Figure 13:
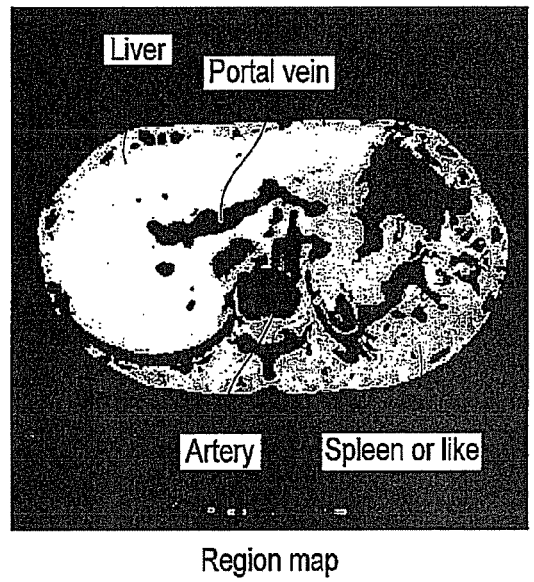
FIG. 13 is a view showing an example of the region map generated in step S17 in FIG. 2.

The AIC map generation unit 124 generates an AIC map (see FIG. 11) corresponding to the liver model based on the residual map corresponding to the liver model (S15). Likewise, the AIC map generation unit 124 generates an AIC map corresponding to the spleen model from the residual map corresponding to the spleen model. As shown in FIG. 12, the AIC map processing unit 125 selects the minimum value between the AIC values of the AIC map corresponding to the liver model and the AIC values of the AIC map corresponding to the other model for each pixel, and generates a minimum AIC map (S16). As shown in FIG. 13, the AIC map processing unit 125 performs clustering/labeling processing and contour extraction processing for the minimum AIC map to generate a region map in which blood vessels and organ regions are segmented (S17). The region map is obtained by segmenting blood vessels and organ regions based on suitability indices corresponding to the respective kinetic models.

Figure 14:
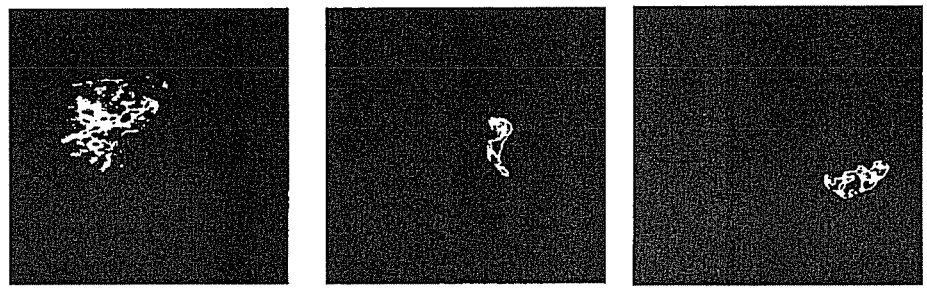
FIG. 14 is a view showing an example of the composite perfusion map generated in step S18 in FIG. 2.
Figure 14:
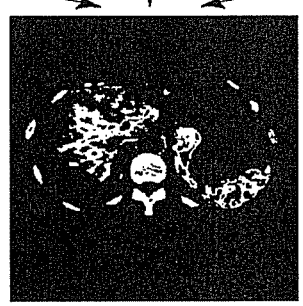

As shown in FIG. 14, the perfusion map combining unit 126 generates a single perfusion map (composite perfusion map) by partly pasting a plurality of perfusion maps in accordance with the region map generated by the AIC map processing unit 125 (S18). The composite perfusion map is displayed in halftone or color on the display device 116 under the control of display control unit 127 (S19).

Figure 15:
FIG. 15 is a view showing various display functions on the composite perfusion map which are executed in steps S20 to S25 in FIG. 2.

In this display operation, the display control unit 127 can execute processing corresponding to each type of display instruction, as indicated by steps S20 to S25 in FIG. 3 and exemplified by FIG. 15. When the operator inputs "instruction to display region segment frame", the display control unit 127 generates region segment frames to segment organ regions in accordance with the region map, superimposes the frames on the composition perfusion map, and displays the resultant map (S20). When the operator inputs "instruction to superimpose and display tomographic images", the display control unit 127 superimposes and displays an arbitrary image of a series of tomographic images, e.g., the tomographic image of the last frame, on a composite perfusion map (or designated perfusion map); or continuously displays the series of tomographic images as a moving image (S21). When the operator inputs "instruction to individually adjust display conditions", the display control unit 127 causes the display device to display, on a display window of a composite perfusion map, operation boxes corresponding to conditions allowing display setting, e.g., a display window adjustment scale and a lookup table selection box, adjusts a display window for the organ region selected by the operator, and switches lookup tables (S22). In this manner, the display control unit 127 can individually adjust display conditions for the respective organ regions.

When the operator designates an arbitrary point on a composite perfusion map, the display control unit 127 displays a TDC corresponding to the designated point as a graph on the same window as that of a composite perfusion map side by side (S23). When the operator sets a region of interest (ROI) on a composite perfusion map, the display control unit 127 generates and displays an average TDC from a plurality of TDCs corresponding to the ROI, and calculates and displays an average perfusion index in the ROI (S24).

When the operator inputs a command "not to display any regions exhibiting low suitability", the display control unit 127 non-displays a composite perfusion map associated with a region exhibiting an AIC value higher than a predetermined threshold on the minimum AIC map (S25). When the operator inputs a command "to clarify blood vessel region", the display control unit 127 generates a mask mark in a unique form such as hatching, which corresponds to a blood vessel region identified on the region map, and superimposes it on the composite perfusion map (S26). At this time, the blood vessel region is excluded from the calculation of the above ROI. This makes it possible to easily check the blood vessel region or recognize a region exhibiting low analysis accuracy, thereby discriminating false positivity.

Simultaneously displaying perfusion maps, which have been individually analyzed and output, in this manner allows easy interpretation and reduces the probability of diagnosis errors. In addition, region segmentation of blood vessels and the respective tissues can individually set optimal analysis conditions and display conditions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
   a storage unit configured to store data of a series of medical images associated with an object;
   a time density curve generation unit configured to generate a plurality of time density curves respectively corresponding to a plurality of pixels from the series of medical images;
   an approximation processing unit configured to approximate a convolution between a specific time density curve of the time density curves and each of response functions respectively having shapes suited to types of kinetic models to each of the time density curves upon adjustment of at least one parameter which each of the kinetic models has; and
   a suitability index map generation unit configured to generate a plurality of types of suitability index maps respectively corresponding to the plurality of types of kinetic models based on a plurality of approximation errors respectively corresponding to the plurality of pixels, which are obtained by the approximation processing unit.

2. The medical image processing apparatus of claim 1, wherein the plurality of types of kinetic models comprise a plurality of transfer functions respectively corresponding to a plurality of organs, and
   each of the plurality of transfer functions is defined based on a relationship between an input of blood and an output of blood in a corresponding organ.

3. The medical image processing apparatus of claim 2, further comprising a perfusion map generation unit configured to generate a plurality of types of perfusion maps respectively corresponding to the plurality of kinetic models based on the parameters.

4. The medical image processing apparatus of claim 3, further comprising a perfusion map combining unit configured to generate a single perfusion map by cutting and pasting the plurality of types of perfusion maps based on the plurality of types of suitability index maps.

5. The medical image processing apparatus of claim 3, further comprising a high suitability index map generation unit configured to generate a high suitability index map representing a spatial distribution of highest suitability index values based on the plurality of types of suitability index maps.

6. The medical image processing apparatus of claim 5, wherein the high suitability index map generation unit generates a segment map indicating segments of the plurality of organs based on the high suitability index map.

7. The medical image processing apparatus of claim 6, wherein the segment map is superimposed and displayed on the signal perfusion map.

8. The medical image processing apparatus of claim 7, wherein the displayed perfusion map differs in display form for each segment in accordance with the segment map.

9. The medical image processing apparatus of claim 7, wherein a marker indicating a region exhibiting a suitability index value less than a threshold on the high suitability index map is superimposed on the display perfusion map.

10. The medical image processing apparatus of claim 7, wherein a portion, of the displayed perfusion map, which corresponds to a region exhibiting a suitability index value less than a threshold on the high suitability index map is set to non-display.

11. The medical image processing apparatus of claim 7, wherein a boundary line of the segment is superimposed on the segment map.

12. The medical image processing apparatus of claim 6, wherein at least one of the suitability index maps is displayed together with at least one of the perfusion maps.

13. A medical image processing apparatus comprising:
a storage unit configured to store data of a series of medical images associated with an object;
a time density curve generation unit configured to generate a plurality of time density curves respectively corresponding to a plurality of pixels from the series of medical images;
an approximation processing unit configured to approximate a convolution between each of a plurality of types of kinetic models and a standard time density curve to each of the plurality of time density curve upon adjustment of at least one parameter which each of the kinetic models has; and
a suitability index map generation unit configured to generate a plurality of types of suitability index maps respectively corresponding to the plurality of types of kinetic models based on an approximation error of the convolution.

\* \* \* \* \*